(12) United States Patent
Matos et al.

(10) Patent No.: US 9,034,640 B2
(45) Date of Patent: May 19, 2015

(54) BIOREACTOR FOR CONTROLLING CELLULAR GROWTH

(75) Inventors: Marvi A. Matos, Seattle, WA (US); William B. Carlson, Seattle, WA (US); Ivan Vesely, Larkspur, CO (US); Yansong Gu, Bellevue, WA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 107 days.

(21) Appl. No.: 13/322,393

(22) PCT Filed: May 12, 2011

(86) PCT No.: PCT/US2011/036262
§ 371 (c)(1),
(2), (4) Date: Nov. 23, 2011

(87) PCT Pub. No.: WO2012/154187
PCT Pub. Date: Nov. 15, 2012

(65) Prior Publication Data
US 2012/0288937 A1  Nov. 15, 2012

(51) Int. Cl.
*C12M 3/06* (2006.01)
*C12M 1/12* (2006.01)
*C12M 1/00* (2006.01)
*C12M 1/42* (2006.01)
*C12M 3/00* (2006.01)

(52) U.S. Cl.
CPC ............... *C12M 25/14* (2013.01); *C12M 21/08* (2013.01); *C12M 23/34* (2013.01); *C12M 29/04* (2013.01); *C12M 35/08* (2013.01)

(58) Field of Classification Search
CPC ...... C12M 21/08; C12M 23/34; C12M 25/14; C12M 29/04; C12M 35/08
USPC .................. 435/297.2–297.5, 397, 401
See application file for complete search history.

(56) References Cited

U.S. PATENT DOCUMENTS 6,899,873 B2   5/2005   Ma et al.
2009/0155908 A1   6/2009   Halberstadt et al.

FOREIGN PATENT DOCUMENTS

JP          61038605 A   *   2/1986
WO     WO-2010/101708          9/2010

OTHER PUBLICATIONS

Atala, A., "Engineering tissues, organs and cells," Journal of Tissue Engineering and Regenerative Medicine, 2007, vol. 1, pp. 83-96.
(Continued)

*Primary Examiner* — William H Beisner
(74) *Attorney, Agent, or Firm* — Foley & Lardner LLP

(57) ABSTRACT

A system includes a first chamber configured to receive a hydrogel and a scaffold comprising a cell, wherein the hydrogel is in fluid communication with the scaffold, and wherein the hydrogel includes a plurality of unidirectional pores. The system also includes a second chamber configured to receive a first fluid and a second fluid, wherein the second chamber includes a wall that separates the first fluid from the second fluid. The system further includes a porous membrane configured to separate the first chamber from the second chamber. The wall is configured to move along the porous membrane as cellular extensions are projected into at least a portion of the plurality of unidirectional pores of the hydrogel.

19 Claims, 5 Drawing Sheets

(56) References Cited

OTHER PUBLICATIONS

Borenstein, J.T. et al., "Microfabrication of three-dimensional engineered scaffolds," Tissue Engineering, 2007, vol. 13, No. 8, pp. 1837-1844.
Cheng, S.Y. et al., "A hydrogel-based microfluidic device for the studies of directed call migration," Lab on a Chip, 2007, vol. 7, No. 6, pp. 763-769.
Cleveland Clinic, "The Spinal Cord and Injury," printed on Oct. 19, 2011, retrieved from http://my.clevelandclinic.org/disorders/spinal_cord_injury/hic_spinal_cord_injury_overview.aspx, 3 pages.
Grayson, W.L. et al., "Biomimetic Approach to Tissue Engineering," Author Manuscript, Semin. Cell Dev. Biol., Aug. 2009, vol. 20, No. 6, pp. 665-673, 16 pages.
International Search Report and Written Opinion for PCT/US2011/036262 mailed Aug. 12, 2011.
Kunze, A. et al., "Micropatterning neural cell cultures in 3D with a multi-layered scaffold," Biomaterials, 2011, vol. 32, pp. 2088-2098.
National Institute of Neurological Disorders and Stroke, "Spinal Cord Injury," printed on Oct. 19, 2011, retrieved from http://www.ninds.nih.gov/disorders/sci/sci.htm, 3 pages.
Prang, P. et al., "The promotion of oriented axonal regrowth in the injured spinal cord by alginate-based anisotropic capillary hydrogels," Biomaterials, 2006, vol. 27, pp. 3560-3569.
Sirkar, K.K., "Membranes, Phase Interfaces, and Separations: Novel Techniques and Membranes—An Overview," Ind. Eng. Chem. Res., Published on Web Jul. 15, 2008, vol. 47, pp. 5250-5266.
Slaughter, B.V. et al., "Hydrogels in Regenerative Medicine," Adv. Mater., 2009, vol. 21, pp. 3307-3329.
International Preliminary Report on Patentability in PCT/US2011/036262 dtd Nov. 21, 2013 (5 pages).

\* cited by examiner

US 9,034,640 B2

BIOREACTOR FOR CONTROLLING CELLULAR GROWTH

CROSS-REFERENCE TO RELATED APPLICATIONS

The present application is a U.S. national stage application under 35 U.S.C §371 of International Application No. PCT/US2011/036262, filed on May 12, 2011, the entire content of which is incorporated herein by reference in its entirety.

BACKGROUND

The following description is provided to assist the understanding of the reader. None of the information provided or references cited is admitted to be prior art.

The field of tissue engineering has recently emerged as a strong player in the field of regenerative medicine. Due to their unique properties, hydrogels are ideal candidates for use in tissue engineering applications. Hydrogels are relatively easy to synthesize and they can be biocompatible. Hydrogels also allow for the adsorption of biologically active molecules that can influence cellular behavior as well as allow for the mass transport of nutrients and waste. Their similarities with the extra-cellular matrix in structure and sometimes in chemical composition, and their ability to sustain viable and proliferating cells, are desired qualities that hydrogels exhibit for the application of tissue constructs. Their high promise have driven scientists to synthesize structures that are used to mimic tissues that play central roles in our bodies, such as liver tissue, neural tissue, etc.

SUMMARY

An illustrative system includes a first chamber configured to receive a hydrogel and a scaffold comprising a cell, wherein the hydrogel is in fluid communication with the scaffold, and wherein the hydrogel includes a plurality of unidirectional pores. The system also includes a second chamber configured to receive a first fluid and a second fluid, wherein the second chamber includes a wall that separates the first fluid from the second fluid. The system further includes a porous membrane configured to separate the first chamber from the second chamber. The wall is configured to move along the porous membrane as cellular extensions are projected into at least a portion of the plurality of unidirectional pores of the hydrogel.

An illustrative process includes placing a scaffold and a hydrogel in fluid communication with the scaffold into a first chamber of a tissue construct generating system, wherein the hydrogel includes a plurality of unidirectional pores. A first fluid and a second fluid are placed into a second chamber, wherein the second chamber includes a wall that separates the first fluid from the second fluid, and wherein the first chamber is separated from the second chamber by a porous membrane. The wall is moved along the porous membrane as a cell from the scaffold extends projections into at least one of the plurality of unidirectional pores of the hydrogel.

Another illustrative system includes first means for receiving a scaffold and a hydrogel, wherein the hydrogel includes a plurality of unidirectional pores. The system also includes second means for receiving a first fluid and a second fluid, wherein the second means for receiving the first fluid and the second fluid includes a first means for separating the first fluid from the second fluid. The system further includes second means for separating the first means for receiving from the second means for receiving, wherein the first means for separating is configured to move along the second means for separating as cells are grown in at least a portion of the plurality of unidirectional pores of the hydrogel.

The foregoing summary is illustrative only and is not intended to be in any way limiting. For example, while hydrogels with unidirectional pores are envisioned to help in the guidance for cell growth, hydrogels with other characteristics can also be used. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
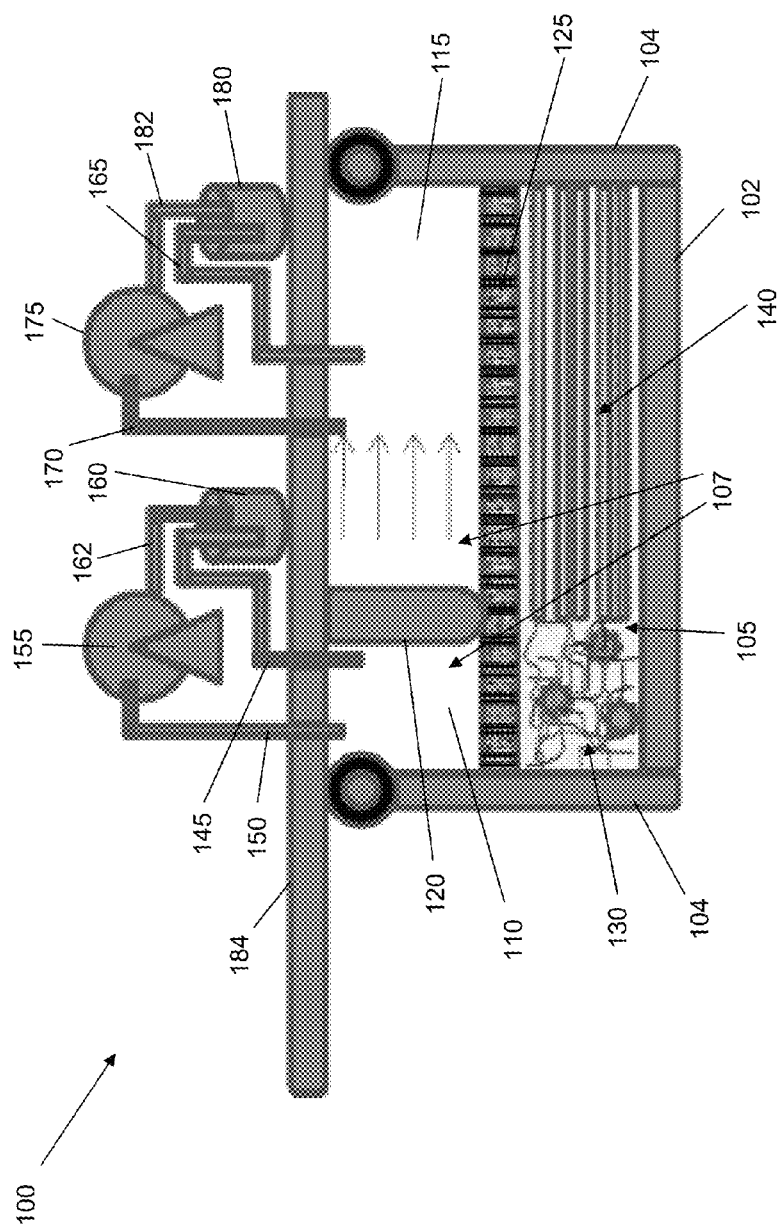
FIG. 1 is a cross sectional side view of a bioreactor for controlling growth of cellular projections in accordance with a first illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

FIG. 1 is a diagram of a bioreactor 100 for controlling growth of cellular projections in accordance with an illustrative embodiment. As used herein, "cellular projections" refers to membrane-cytoskeleton-based structures extending from a cell body. Cellular projections include but are not limited to villi, microvilli, pseudopodia, filopodia, lamellipodia, growth cones, flagella, cilia, acrosomes, axons, and dendrites. Bioreactor 100 can also be used to understand how cells respond to changes in environmental conditions and whether cellular differentiation can be influenced by exposure to a particular substance of interest. Any substance of interest may be used, including but not limited to growth factors, neurotransmitters, cytokines, hormones, and ions. Growth factors of interest may include but are not limited to fibroblast growth factor (FGF), nerve growth factor (NGF), and vascular endothelial growth factor (VEGF). Neurotransmitters of interest may include but are not limited to glutamate, aspartate, D-serine, γ-aminobutyric acid (GABA), glycine, dopamine (DA), norepinephrine (noradrenaline), epinephrine (adrenaline), histamine, serotonin (SE, 5-HT), acetylcholine (ACh), adenosine, anandamide, and nitric oxide. Cytokines of interest may include but are not limited to interleukins (IL-1, IL-2, etc), and chemokines (CCL1, CCL15). Hormones of interest may include but are not limited to epinephrine, TRH, vasopressin, luteinizing hormone, linoleic acid, arachidonic acid, thyroxine, and adrenaline. Ions of interest may include but are not limited to sodium, potassium, chloride, bicarbonate, and calcium. Any cell type may be grown in bioreactor 100, including but not limited to neuronal cells, connective tissue, organs such as liver and pancreas, muscle, and endothelial cells.

In an illustrative embodiment, one or more cell types can be placed in bioreactor 100. In an illustrative embodiment, the cells can be used to form any type of tissue of which in at least one or more portions or layers there is largely unidirectional growth of cellular projections. Bioreactor 100 is formed by a bottom wall 102, sidewalls 104, and an upper wall 184. In an illustrative embodiment, bottom wall 102, sidewalls 104, and upper wall 184 are formed from a suitable biocompatible material as known to those of skill in the art. In one embodiment, the biocompatible material includes but is not limited to an opaque or transparent plastic, a glass, or a metal such as stainless steel. Use of a transparent biocompatible material to form bioreactor 100 can help facilitate visual inspection and measurements of the cells during cell culture. Bioreactor 100 may include but is not limited to a cell growth chamber 105, a fluid chamber 107, and a membrane 125 that separates cell growth chamber 105 from fluid chamber 107.

Cell growth chamber 105 may be formed by the interior wall of the bottom wall 102, the interior walls of the portions of the side walls 104 located between the bottom wall 102 and the membrane 125, and the lower edge of the membrane 125. The cell growth chamber walls can be made from or coated with a biocompatible material as known to those of skill in the art. In one embodiment, the biocompatible material can be an opaque or transparent plastic, glass, or a non-reactive metal such as stainless steel. Materials are selected based on the characteristics of the cell type in use as known to those of skill in the art. The materials may be sterilizable, reusable, or disposable based on the characteristics of the cell type in use and the preferences of the operator. In one embodiment, the dimensions of cell growth chamber 105 can range from approximately 1-2 cubic centimeters ($cm^3$) to approximately 500 $cm^3$. In alternative embodiments, cell growth chamber 105 can be smaller than 1 $cm^3$ or larger than 500 $cm^3$. In an illustrative embodiment, the dimensions of cell growth chamber 105 are selected based on the characteristics of the cell type in use and/or any instruments which are used to view or otherwise measure cellular projection growth.

Cell growth chamber 105 includes one or more cell scaffolds 130. As used herein, "cell scaffold" refers to any material in which cells can be suspended or to which cells can adhere. In an illustrative embodiment, the cell scaffold material is biologically derived, such as but not limited to, collagen, alginate, fibrin, dextran, chitosan, agarose, hyaluronan, cellulose and gelatin. In an alternative embodiment, the cell scaffold material is synthetic, such as but not limited to poly(ethylene glycol) (PEG), poly(ethylene glycol)-poly(lactic acid) (PEG-PLA), poly(acrylic acid) (PAA), poly(2-hydroxymethyl methacrylate) (PHEMA), polyethersulfone (PES), poly(lactide-coglycolide) (PLGA) and poly(vinyl alcohol). In an alternative embodiment, the cell scaffold material is a combination or hybrid of a natural polymer and a synthetic polymer. Other cell scaffolds include but are not limited to, silk fibroin, heparin-based hydrogels, microcarrier-based scaffolds, vegetable-based scaffolds, galactosylated polymer substrates, inverse colloidal crystal (ICC) substrates, dendrimer grafted substrates, growth factor presenting substrates, nanofibrous substrates, chemo-biologically synthesized substrates, and derivatives thereof. Selection of scaffold material is based on the characteristics of the cell type in use and the preferences of the operator. In an illustrative embodiment, the volume of cell scaffolds 130 can be between 5 $cm^3$ and 500 $cm^3$. Alternatively, a smaller or larger volume may be used. In an illustrative embodiment, a given scaffold may be used to grow a single type of cell or multiple cell types. In an alternative embodiment, multiple scaffolds of differing materials may be used to simultaneously culture different types of cells in bioreactor 100. In an illustrative embodiment, cell scaffolds 130 can be placed into cell growth chamber 105 through, for example, a door or other opening (not shown) in one of sidewalls 104 of bioreactor 100. The skilled artisan will understand that cell growth chamber 105 contains a cell culture media suitable for the specific cell-type being cultured. Illustrative cell culture media include but are not limited to DMEM, DMEM/F12 media, Ham's F-10 media, Ham's F-12 media, medium 199, MEM, RPMI 1640 media, and others known in the art.

In an illustrative embodiment, cell scaffolds 130 are hydrogel-cell composites that include cells encapsulated by a hydrogel. Any cell type may be used, including but not limited to neuronal, muscle and endothelial cells, cells forming tissues such as but not limited to connective tissue, and cells forming organs such as but not limited to liver and pancreas. The hydrogel can include, but is not limited to, an alginate, a collagen, a 2-hydroxyethyl methacrylate-co-methyl methacrylate (PHEMA-MMA) hydrogel, or a variety of other hydrogels known to those of skill in the art. Additional examples of cells and corresponding hydrogels can be found in an article titled "Hydrogels in Regenerative Medicine" by Slaughter et al. (from Adv. Mater. 2009, 21, 3307-3329), the entire disclosure of which is incorporated herein by reference. In an illustrative embodiment, cells are encapsulated in a hydrogel prior to placement in cell growth chamber 105 through mixing of the cells with the hydrogel prior to polymerization of the hydrogel. In alternative embodiments, cells are seeded into a porous scaffold material by centrifugation, agitation, exposure to elevated atmospheric pressure, use of magnetic particles and magnetic force, or other methods known in the art.

Cell growth chamber 105 also includes a plurality of scaffold materials. In an illustrative embodiment, the scaffold comprises hydrogel constructs 140. In an illustrative embodiment, hydrogel constructs 140 may be alginate-based hydrogels that have unidirectional pores, which act as tubes through which cellular projections can grow. In other embodiments, hydrogel constructs 140 are substituted for other scaffold materials compatible with the embodiment. Other examples of scaffold materials include but are not limited to hydroxyapatite-based porous scaffolds, collagen-based scaffolds and poly(caprolactone)-based scaffolds. In an illustrative embodiment, unidirectional pores are used to organize neuronal cell projections. In another illustrative embodiment, unidirectional pores are used to organize vasculature growth. In an alternative embodiment, hydrogel constructs 140 may be a random network of pores. Hydrogel constructs 140 can be made according to any method known to those skilled the art, and the polymerization technique used can depend on the actual material used. Examples of hydrogel constructs can be found in an article titled "Hydrogels in Regenerative Medicine" by Slaughter et al. (from Adv. Mater. 2009, 21, 3307-3329), the entire disclosure of which is incorporated herein by reference.

Fluid chamber 107 includes a first fluid chamber 110, a second fluid chamber 115, and a wall 120 which separates first fluid chamber 110 from second fluid chamber 115. Fluid chamber 107 is formed by the upper edge of the membrane 125, portions of the internal walls of side walls 104 located between the membrane 125 and the upper wall 184, and the internal face of upper wall 184. Fluid chamber 107 can be made from or coated with a suitable biocompatible or non-toxic material such as, but not limited to, glass, plastic, stainless steel, etc. In an illustrative embodiment, fluid chamber 107 can have a volume of between 1 $cm^3$ and 500 $cm^3$. In alternative embodiments, the volume of fluid chamber 107 may be less than 1 $cm^3$ or greater than 500 $cm^3$.

In an illustrative embodiment, first fluid chamber 110 is configured to receive a first fluid and second fluid chamber 115 is configured to receive a second fluid. In another illustrative embodiment, the first fluid and the second fluid have different concentrations (or molarities) of a substance of interest such that there is a concentration differential between first fluid chamber 110 and second fluid chamber 115. As an example, the first fluid may be cell culture media having a low concentration of a substance of interest relative to the second fluid, and the second fluid may be cell culture media having a high concentration of a substance of interest relative to the first fluid. Alternatively, the first fluid may have the high concentration and the second fluid may have the low concentration. In one illustrative embodiment, saline having a concentration of approximately 150 millimolar (mM) can be used as either the first fluid or the second fluid. In another illustrative embodiment, the sodium concentration of either the first fluid or the second fluid can be approximately 170 mM, which is the approximate sodium concentration in a human spinal cord under normal conditions. In an illustrative embodiment, the concentration of sodium used for the first and second fluids can be between 50 mM and 500 mM. In alternative embodiments, the sodium concentration can be less than 50 mM or greater than 500 mM. In an alternative embodiment, sodium may not be used or may be used in combination with one or more additional substances of interest. For example, the first fluid and/or the second fluid may include potassium, calcium, manganese, or any other ion to form the concentration gradient. In one embodiment, Forskolin can be used to form the concentration gradient. The skilled artisan will understand that any substance of interest may be used to generate the concentration gradient, including but not limited to ions, growth factors, neurotransmitters, cytokines, and hormones. Growth factors of interest may include but are not limited to fibroblast growth factor (FGF), nerve growth factor (NGF), and vascular endothelial growth factor (VEGF). Neurotransmitters of interest may include but are not limited to glutamate, aspartate, D-serine, γ-aminobutyric acid (GABA), glycine, dopamine (DA), norepinephrine (noradrenaline), epinephrine (adrenaline), histamine, serotonin (SE, 5-HT), acetylcholine (ACh), adenosine, anandamide, and nitric oxide. Cytokines of interest may include but are not limited to interleukins (IL-1, IL-2, etc), and chemokines (CCL1, CCL15). Hormones of interest may include but are not limited to epinephrine, TRH, vasopressin, luteinizing hormone, linoleic acid, arachidonic acid, thyroxine, and adrenaline. Ions of interest may include but are not limited to sodium, potassium, chloride, bicarbonate, and calcium.

First fluid chamber 110 includes an inlet conduit 145 for introducing the first fluid into first fluid chamber 110 and an outlet conduit 150 for drawing the first solution out of first fluid chamber 110. A pump 155 is used to circulate the first fluid between first fluid chamber 110 and a reservoir 160 containing the first fluid such that the concentration of the first fluid is maintained at a desired level. A pump conduit 162 connects pump 155 and reservoir 160. Pump 155 can be any type of fluid pump known to those of skill in the art. Reservoir 160 can be made from a suitable biocompatible material such as, but not limited to, glass, plastic, stainless steel, etc. In one embodiment, reservoir 160 can have a volume of between 100 milliliters (mL) and 5 liters (L) depending on the size of fluid chamber 110 and the concentrations used for the stimulant. In an alternative embodiment, the volume of reservoir 160 may be less than 100 mL or greater than 5 L. Pump conduit 162 can be made from a suitable biocompatible material such as, but not limited to, glass, plastic, stainless steel, etc.

In an illustrative embodiment, the first fluid can be continuously circulated between first fluid chamber 110 and reservoir 160. In an alternative embodiment, the first fluid may be periodically circulated between first fluid chamber 110 and reservoir 160. In one embodiment, the concentration of the first fluid can be monitored to determine if the concentration of one or more components goes above or below a desired level. If the concentration of one or more components of the first fluid is too high or too low, the first fluid in reservoir 160 can be replaced. In one embodiment, a conductivity meter can be used to monitor the first fluid. Any type of conductivity meter known to those of skill in the art can be used. The monitoring can be performed automatically by a computing system or manually by a user, depending on the embodiment. In another embodiment, a pH meter can be used to monitor the first fluid. Any type of pH meter known to those of skill in the art can be used. The monitoring can be performed automatically by a computing system or manually by a user, depending on the embodiment. The skilled artisan will understand that any aspect of the fluid may be monitored such as pH, nutrient content, and the like.

Second fluid chamber 115 includes an inlet conduit 165 for introducing the second fluid into second fluid chamber 115 and an outlet conduit 170 for drawing the second solution out of second fluid chamber 115. A pump 175 is used to circulate the second fluid between second fluid chamber 115 and a reservoir 180 containing the second fluid such that the concentration of the second fluid is maintained at a desired level. Reservoir 180 can be made from a suitable biocompatible material such as, but not limited to, glass, plastic, stainless steel, etc. A pump conduit 182 connects pump 175 and reservoir 180. Pump 175 can be any type of fluid pump known to those of skill in the art. Pump conduit 182 can be made from a suitable biocompatible material such as, but not limited to, glass, plastic, stainless steel, etc. In one embodiment, the second fluid can be continuously circulated between second fluid chamber 115 and reservoir 180. In an alternative embodiment, the second fluid may be periodically circulated between second fluid chamber 115 and reservoir 180. In one embodiment, the concentration of the second fluid can be monitored to determine if the concentration goes above or below a desired level. If the concentration of the second fluid is too high or too low, the second fluid in reservoir 180 can be replaced. In one embodiment, a conductivity meter can be used to monitor the second fluid. Any type of conductivity meter known to those of skill in the art can be used. The monitoring can be performed automatically by a computing system or manually by a user, depending on the embodiment.

In an illustrative embodiment, wall 120 separates first fluid chamber 110 and second fluid chamber 115 such that the first fluid and the second fluid are separated from one another. Wall 120 is in contact with upper wall 184 of bioreactor 100 such that wall 120 is able to slide along upper wall 184 from left to right (or vice versa) in the view of FIG. 1. Wall 120 is in further contact with membrane 125, such that the bottom end of wall 120 slides along membrane 125 as wall 120 is moved. As wall 120 moves along upper wall 184 and membrane 125, the first fluid and the second fluid chambers remain separated from one another due to fluid tight contacts at the 120-184 and 120-125 junctures. In an illustrative embodiment, wall 120 is made of rubber or a rubber-like material such that when contacted with membrane 125 a fluid-tight junction is formed. In an illustrative embodiment, the entire wall 120 is made of rubber or a rubber-like material. In an alternative embodiment, the bottom portion of wall 120 is made of rubber or a rubber-like material. In an alternative embodiment, wall 120 is made of some other impermeable material known to those of skill in the art. In an illustrative embodiment, wall 120 is made of a biocompatible material. In an illustrative embodiment, the bottom end of wall 120 is rounded or tapered to help facilitate the sliding of wall 120 along membrane 125.

Membrane 125 can be made from a porous, permeable, or semi-permeable material such that a substance of interest may pass from second fluid chamber 115 into hydrogel 140 and generate a concentration gradient across hydrogel 140. The terms "porous" and "permeable" refer to generally membranes that allow substances to pass through, as opposed to impermeable barriers that do not. The term "semi-permeable" refers to membranes that allow only certain molecules to pass through. Whether a given molecule passes through a given semi-permeable membrane depends on its physical properties, including but not limited to size, solubility, and charge. The membrane can be made from artificial polymers, such as but not limited to nanoporous cellulose, polypropylene, polystyrene, etc. Additional examples of membranes and materials that can be used as membrane 125 can be found in an article titled "Membranes, Phase Interfaces, and Separations: Novel Techniques and Membranes—An Overview" (Ind. Eng. Chem. Res. 2008, 47, 5250-5266), the entire disclosure of which is incorporated herein by reference.

Given the permeable nature of membrane 125, cell growth chamber 105 (which includes the cell scaffolds and hydrogel structures) can include fluid that passes through the membrane from fluid chamber 110. Likewise, cell growth chamber 105 can include fluid that passes through the membrane from fluid chamber 115. As such, the bioreactor 100 can include a first fluid species in chamber 110, a second fluid species in chamber 115, and a third fluid species in chamber 105 that represents a combination of the first and second fluids.

In illustrative embodiments, a substance of interest passes from fluid chamber 115, through semi-permeable membrane 125, and into hydrogel 140 to form a concentration gradient across the perpendicular axis of hydrogel 140. The presence of a substance of interest in hydrogel 140 serves as a stimulant to cells residing in chamber 105 to extend cellular projections into hydrogel 140. As the projections grow (from left to right) within hydrogel 140, wall 120 is moved from left to right as shown in FIG. 1 such that the bottom end of wall 120 remains over the leading (or growing) edge of the projections. As a result, the concentration gradient formed across hydrogel 140 moves along with the leading edge of the projections and stimulates continued, unidirectional growth as known to those of skill in the art.

Wall 120 can be moved automatically by a motor or other actuator or manually by an operator of bioreactor 100, depending on the embodiment. In one embodiment, software such as Labview® can be used to automatically move wall 120 based on cellular projection measurements and predetermined thresholds. As such, wall 120 can automatically be moved a distance once the growth of cellular projections exceeds a given threshold. In an alternative embodiment, cellular projection growth can be manually monitored using an optical instrument, and wall 120 can be automatically or manually moved based on the manual monitoring. Movement of wall 120 is described in more detail with reference to FIG. 5.

In an illustrative embodiment, the cells grown in bioreactor 100 can be neural stem cells that are used to generate elongated engineered tissue. The use of elongated hydrogel constructs 140 with unidirectional pores promotes the development of elongated axons or other cellular projections. As such, the engineered tissue can be used in spinal cord injuries and other applications in which elongated cells are desirable. The bioreactor can also be used to develop engineered tissue for use in, but not limited to, muscle growth, heart valve repair/replacement, vascular grafts, etc.

Figure 2B:
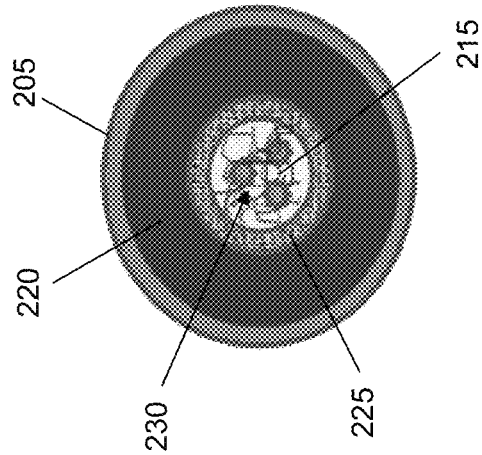
FIG. 2B is a cross sectional end view of the bioreactor for controlling growth of cellular projections in accordance with a second illustrative embodiment.
Figure 2A:
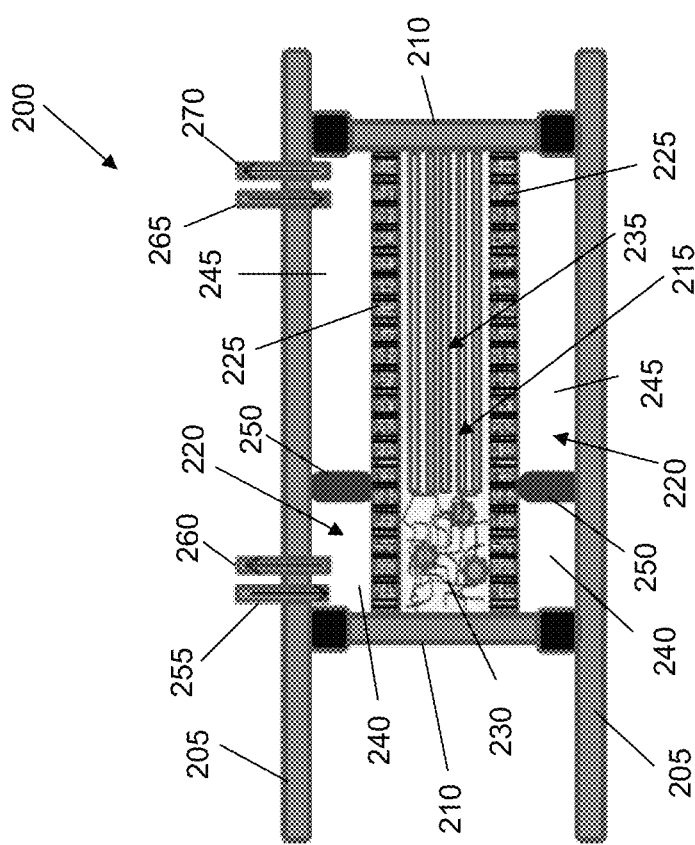
FIG. 2A is a cross sectional side view of a bioreactor for controlling growth of cellular projections in accordance with a second illustrative embodiment.

FIG. 2A is a cross sectional side view of a bioreactor 200 for controlling cellular growth in accordance with a second illustrative embodiment. FIG. 2B is a cross sectional end view of bioreactor 200 in accordance with an illustrative embodiment. As illustrated by the end view of FIG. 2B, bioreactor 200 is constructed in the form of concentric circles. Outside of its structural configuration, bioreactor 200 is similar in operation to bioreactor 100 described with reference to FIG. 1. Bioreactor 200 is formed by a sidewall 205 that is in the shape of a cylinder, and end walls 210. Bioreactor 200 includes a cell growth chamber 215, a fluid chamber 220, and a membrane 225 that separates cell growth chamber 215 from fluid chamber 220.

Cell growth chamber 215 can be made from a biocompatible material as known to those of skill in the art. In one embodiment, the biocompatible material can be an opaque or transparent plastic, a glass, or a metal such as stainless steel. Materials are selected based on the characteristics of the cell type in use as known to those of skill in the art. The materials may be sterilizable, reusable, or disposable based on the characteristics of the cell type in use and the preferences of the operator. Cell growth chamber 215 includes a plurality of cell scaffolds 230. The skilled artisan will understand that cell growth chamber 215 necessarily contains a cell culture media suitable for the specific cell-type being cultured. Illustrative cell culture media include but are not limited to DMEM media, DMEM/F12 media, Ham's F-10 media, Ham's F-12 media, medium 199, MEM, RPMI 1640 media, and others known in the art.

In an illustrative embodiment, cell scaffolds 230 can be placed into cell growth chamber 215 through a door or other opening in an end wall 210 of bioreactor 200. In an illustrative embodiment, cell scaffolds 230 are hydrogel-cell composites that include cells encapsulated by a hydrogel. Any cell type may be grown in bioreactor 200, including but not limited to neuronal cells, connective tissue, organs such as liver and pancreas, muscle, and endothelial cells. In an illustrative embodiment, one or more cell types can be placed in bioreactor 200. The hydrogel can be an alginate, a collagen, a 2-hydroxyethyl methacrylate-co-methyl methacrylate (PHEMA-MMA) hydrogel, or other hydrogels known to those of skill in the art. Cell growth chamber 215 also includes a plurality of hydrogel constructs 235. In an illustrative embodiment, hydrogel constructs 235 have unidirectional pores. As such, hydrogel constructs 235 act as tubes through which projections of the cells in cell scaffolds 230 can grow.

Fluid chamber 220 includes a first fluid chamber 240, a second fluid chamber 245, and a wall 250 which separates first fluid chamber 240 from second fluid chamber 245. In an illustrative embodiment, first fluid chamber 240 is configured to receive a first fluid and second fluid chamber 245 is configured to receive a second fluid. In another illustrative embodiment, the first fluid and the second fluid have different concentrations (or molarities) of a given chemical such that there is a concentration gradient between first fluid chamber 240 and second fluid chamber 245. First fluid chamber 240 includes an inlet conduit 255 for introducing the first fluid into first fluid chamber 240 and an outlet conduit 260 for drawing the first solution out of first fluid chamber 240. A pump (not shown) can be used to circulate the first fluid between first fluid chamber 240 and a reservoir (not shown) containing the first fluid such that the concentration of the first fluid is maintained at a desired level. In one embodiment, the first fluid can be continuously circulated between first fluid chamber 240 and the reservoir. In an alternative embodiment, the first fluid may be periodically circulated between first fluid chamber 240 and the reservoir. In one embodiment, the concentration of the first fluid can be monitored to determine if the concentration goes above or below a desired level. If the concentration of the first fluid is too high or too low, the first fluid in the reservoir can be replaced. The first fluid can be monitored using any method known to those of skill in the art.

Second fluid chamber 245 includes an inlet conduit 265 for introducing the second fluid into second fluid chamber 245 and an outlet conduit 270 for drawing the second solution out of second fluid chamber 245. A pump (not shown) can be used to circulate the second fluid between second fluid chamber 245 and a reservoir (not shown) containing the second fluid such that the concentration of the second fluid is maintained at a desired level. The pump used can be any type of fluid pump known to those of skill in the art. In one embodiment, the second fluid can be continuously circulated between second fluid chamber 245 and the reservoir. In an alternative embodiment, the second fluid may be periodically circulated between second fluid chamber 245 and the reservoir. In one embodiment, the concentration of the second fluid can be monitored to determine if the concentration goes above or below a desired level. If the concentration of the second fluid is too high or too low, the second fluid in the reservoir can be replaced. The second fluid can be monitored using any method known to those of skill in the art.

In an illustrative embodiment, wall 250 separates first fluid chamber 240 and second fluid chamber 245 such that the first fluid and the second fluid are separated from one another. In the embodiment of FIG. 2, wall 250 is doughnut-shaped and has an outer edge (or outer diameter) and an inner edge (or inner diameter). The outer edge of wall 250 is in contact with side wall 205 of bioreactor 200 such that wall 250 is able to slide along side wall 205 from left to right (or vice versa) in the view of FIG. 2A. Wall 250 can be made of a rubber or other impermeable material known to those of skill in the art. In an illustrative embodiment, wall 250 is made of a biocompatible material. The inner edge of wall 250 is in contact with membrane 225 such that the inner edge of wall 250 slides along membrane 225 as wall 250 is moved. In an illustrative embodiment, the inner edge of wall 250 may be rounded or tapered to help facilitate the sliding of wall 250 along membrane 225.

Membrane 225 can be made from a porous or permeable material such that a substance of interest may pass from second fluid chamber 245 into hydrogel 235 and generate a concentration gradient across hydrogel 235. The terms "porous" and "permeable" refer to generally membranes that allow substances to pass through, as opposed to impermeable barriers that do not. The term "semi-permeable" refers to membranes that allow only certain molecules to pass through. Whether a given molecule passes through a given semi-permeable membrane depends on its physical properties, including but not limited to size, solubility, and charge. The membrane can be made from artificial polymers, such as but not limited to nanoporous cellulose, polypropylene, polystyrene, etc. Additional examples of membranes and materials that can be used as membrane 125 can be found in an article titled "Membranes, Phase Interfaces, and Separations: Novel Techniques and Membranes—An Overview" (Ind. Eng. Chem. Res. 2008, 47, 5250-5266), the entire disclosure of which is incorporated herein by reference.

The presence of the substance of interest in hydrogel 235 serves as a stimulant to cells residing in chamber 215 to extend cellular projections into hydrogel 235. As the projections grow (from left to right) within hydrogel 235, wall 250 is moved from left to right as shown in FIG. 2A such that the inner edge of wall 250 remains over the leading edge of the projections. As a result, the concentration gradient formed across hydrogel 235 moves along with the leading edge of the projections, stimulating continued, unidirectional growth as known to those of skill in the art. Wall 250 can be moved automatically by a motor or other actuator or manually by an operator of bioreactor 200, depending on the embodiment.

The skilled artisan will understand that any substance of interest may be used to generate the concentration gradient, including but not limited to ions, growth factors, neurotransmitters, cytokines, and hormones. Growth factors of interest may include but are not limited to fibroblast growth factor (FGF), nerve growth factor (NGF), and vascular endothelial growth factor (VEGF). Neurotransmitters of interest may include but are not limited to glutamate, aspartate, D-serine, γ-aminobutyric acid (GABA), glycine, dopamine (DA), norepinephrine (noradrenaline), epinephrine (adrenaline), histamine, serotonin (SE, 5-HT), acetylcholine (ACh), adenosine, anandamide, and nitric oxide. Cytokines of interest may include but are not limited to interleukins (IL-1, IL-2, etc), and chemokines (CCL1, CCL15). Hormones of interest may include but are not limited to epinephrine, TRH, vasopressin, luteinizing hormone, linoleic acid, arachidonic acid, thyroxine, and adrenaline. Ions of interest may include but are not limited to sodium, potassium, chloride, bicarbonate, and calcium. Any cell type may be grown in bioreactor 200, including but not limited to neuronal cells, connective tissue, organs such as liver and pancreas, muscle, and endothelial cells.

Figure 3:
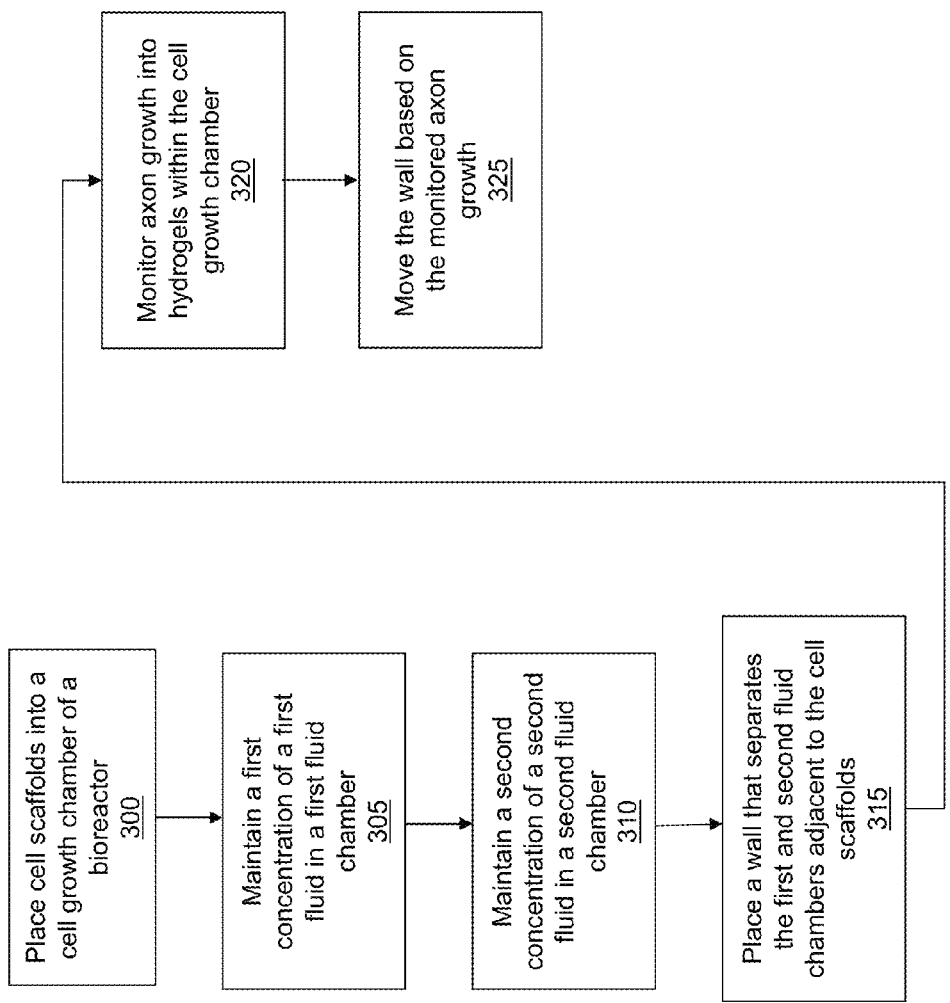
FIG. 3 is a flow diagram illustrating operations performed by a bioreactor in accordance with an illustrative embodiment.

FIG. 3 is a flow diagram illustrating operations performed using a bioreactor in accordance with an illustrative embodiment. In alternative embodiments, fewer, additional, and/or different operations may be performed. Also, the use of a flow diagram is not meant to be limiting with respect to the order of the operations performed. Cells together with cell scaffold material are placed into a cell growth chamber of a bioreactor in an operation 300. In an illustrative embodiment, the bioreactor can be bioreactor 100 described with reference to FIG. 1 or bioreactor 200 described with reference to FIG. 2. The cell scaffolds can be hydrogel-cell composites that include cells encapsulated by a hydrogel. Any cell type may be used, including but not limited to neuronal cells, connective tissue, organs such as liver and pancreas, muscle, and endothelial cells. The hydrogel can be an alginate, a collagen, a 2-hydroxyethyl methacrylate-co-methyl methacrylate (PHEMA-MMA) hydrogel, or other hydrogels known to those of skill in the art. The cell growth chamber can also include a plurality of hydrogel constructs that have unidirectional pores. As such, the hydrogel constructs act as tubes through which projections of the cells in cell scaffolds can grow.

A first concentration of a first fluid is maintained in a first fluid chamber in an operation 305. A second concentration of a second fluid is maintained in a second fluid chamber in an operation 310. As such, the first fluid and the second fluid have different concentrations (or molarities) of a given chemical such that there is a concentration gradient between the first fluid chamber and the second fluid chamber. As an example, the first fluid may be an ionic solution having a low concentration of sodium and the second fluid may be an ionic solution having a high concentration of sodium. Alternatively, the first fluid may have the high concentration and the second fluid may have the low concentration. Any substance of interest may be used to generate the concentration gradient, including but not limited to ions, growth factors, hormones, or other biological molecules.

The first fluid chamber and the second fluid chamber are separated by a movable wall. A permeable or semi-permeable membrane separates the cell growth chamber from the first and second fluid chambers. The moveable wall is initially positioned above the cells and cell scaffold material in an operation 315. As such, the wall is in contact with the membrane, which serves as a barrier between the moveable wall and the cell growth chamber.

Growth of cells within the cell scaffolds is monitored in an operation 320. The growth can be monitored manually by visually inspecting cellular projections with the naked eye or with a microscope or other magnification device. Alternatively, growth of cellular projections may be monitored automatically by sensors or any other method known to those of skill in the art. The moveable wall is re-positioned based on the extent of cellular projection growth in an operation 325. In an illustrative embodiment, the wall is re-positioned to be continually aligned with the leading (or growing) edge of the cellular projections as they extend into the hydrogel constructs. As a result, the concentration gradient formed across the hydrogel construct is relocated to a point more distant from the cells and cell scaffold material. Re-positioning of the gradient facilitates continued, unidirectional growth of cellular projections in the direction of the gradient.

Figure 4:
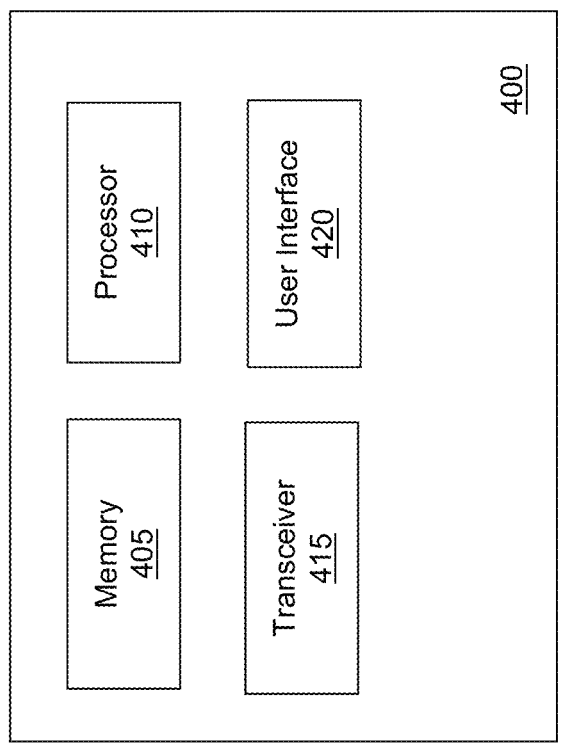
FIG. 4 is a block diagram illustrating a computer system for controlling a bioreactor in accordance with an illustrative embodiment.

FIG. 4 is a block diagram illustrating a computer system 400 for controlling a bioreactor in accordance with an illustrative embodiment. Computer system 400 can be in wired or wireless communication with the bioreactor, depending on the embodiment. Computer system 400 includes a memory 405, a processor 410, a transceiver 415, and a user interface 420. Memory 405 can be any type of computer memory known to those of skill in the art. In an illustrative embodiment, memory 405 can store computer-readable instructions that, when executed, cause a bioreactor to perform any of the operations described herein. Processor 410, which can be any type of processor known to those of skill in the art, can be configured to execute the computer-readable instructions stored in memory 405. Transceiver 415 can be used to transmit and receive data from remote sources. In one embodiment, transceiver 415 is configured to receive instructions for controlling the bioreactor from a remote location. User interface 4720 allows an operator to interact with and control computer system 400 and/or the bioreactor. User interface 420 can include a keyboard, a display, a mouse, a touch screen, etc.

Figure 5:
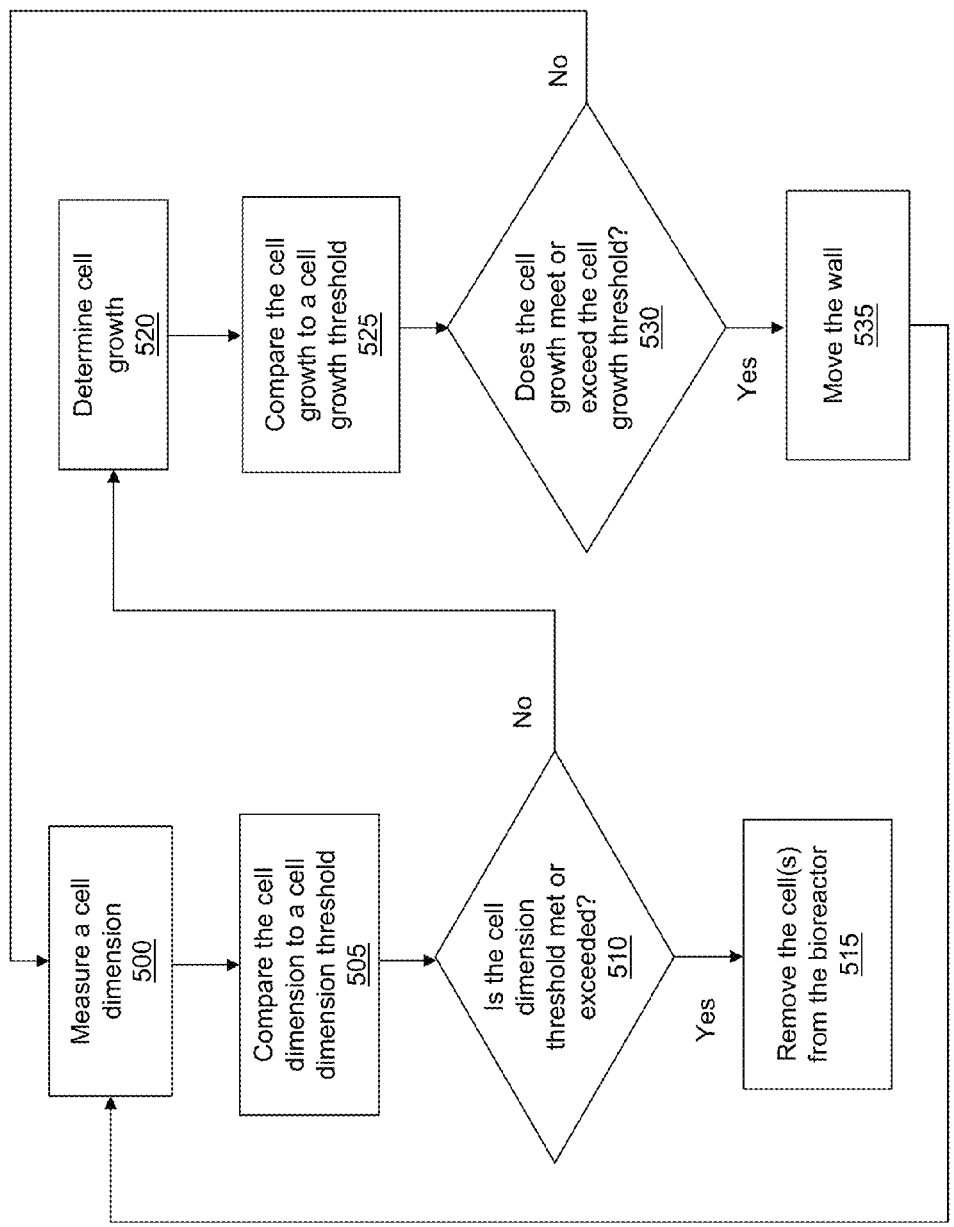
FIG. 5 is a flow diagram illustrating operations performed during cell culture in accordance with an illustrative embodiment.

FIG. 5 is a flow diagram illustrating operations performed during cell culture in accordance with an illustrative embodiment. In alternative embodiments, fewer, additional, and/or different operations may be performed. Also, the use of a flow diagram is not meant to be limiting with respect to the order of the operations performed. The operations of FIG. 5 can be performed automatically by a computer system such as computer system 400, or manually depending on the embodiment. A cell dimension is measured in an operation 500. In an illustrative embodiment, the cell dimension can be a length of a cell or a length of a portion of a cell such as an axon. In an alternative embodiment, the cell dimension can be a diameter of a portion of the cell, a width of the cell, or any other cell dimension. The cell dimension can be automatically or manually measured using any optical device known to those of skill in the art. The cell measurements can be stored in a computer memory such as memory 405. The cell dimension can be measured for a single cell. Alternatively, the cell dimension can be a calculated average of the cell dimensions of two or more cells. The frequency at which cell measurements are made can depend on the type of cell being grown, and can be seconds apart, minutes apart, hours apart, days apart, etc.

The cell dimension is compared to a cell dimension threshold in an operation 505. The cell dimension threshold can be a value of the cell dimension which indicates that cellular projection growth is complete. The cell dimension threshold can be based on the type of cell being grown and/or the intended use of the grown cells. A determination of whether the cell dimension meets or exceeds the cell dimension threshold is made in an operation 510. If the cell dimension meets or exceeds the cell dimension threshold, cellular projection growth is complete and the cell(s) can be removed from the bioreactor in an operation 515 and used for their intended purpose.

If it is determined that the cell dimension does not meet or exceed the cell dimension threshold, cellular projection growth is determined in an operation 520. The cellular projection growth can be determined based on the measured dimension of a single cell or based on an average measured dimension of two or more cells. In an illustrative embodiment, the cellular projection growth can be determined based on a change in the length or other dimension as compared to a previous measurement. This change can be manually or automatically calculated depending on the embodiment.

The cellular projection growth is compared to a projection growth threshold in an operation 525. The projection growth threshold can be specific to the type of cells being cultured, and can be on the order of picometers, nanometers, micrometers, etc. A determination is made regarding whether the cellular projection growth meets or exceeds the projection growth threshold in an operation 530. If it is determined that the projection growth threshold is met or exceeded, the wall (such as wall 120 or wall 250) is moved in an operation 535. The wall can be moved a distance such that the concentration gradient remains proximate to a growing edge of the cell(s). The distance can be a predetermined distance based on the type of cells being grown. Alternatively, the distance can be a determined distance based on the determined cellular projection growth. The wall can be moved automatically or manually depending on the embodiment.

Once the wall is moved, the cell dimension can again be measured in operation 500 and the process can be repeated. If it is determined that the growth of cellular projections does not exceed or meet the projection growth threshold in operation 530, the wall is not moved and the cell dimension can again be measured in operation 500. In one embodiment, the subsequent measurement of the cell dimension may occur after a delay such as one or more seconds, one or more minutes, one or more hours, one or more days, etc. In an alternative embodiment, the subsequent measurement of the cell dimension may be made immediately after the wall is moved in operation 535 or after the determination is made that the projection growth does not exceed or meet the projection growth threshold in operation 530.

As indicated above, the operations of FIG. 5 can be manually performed or automatically performed by a computer system. In an embodiment in which at least some of the operations of FIG. 5 are automated, a user can be prompted through a user interface (such as user interface 420) to specify whether the operations are to be performed automatically or manually. The user can also use the user interface to enter measured cell dimensions if the measurements are not automatically taken by the computer system, to enter the cell dimension threshold, to enter the projection growth threshold, to enter a distance by which the wall is to be moved if the projection growth exceeds the projection growth threshold, to enter a rate at which the pumps circulate fluid between the reservoirs and the fluid chambers, etc.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A system comprising:
    a bioreactor that comprises:
        a first chamber that includes a hydrogel and a scaffold comprising a cell, wherein the hydrogel is in fluid communication with the scaffold, and wherein the hydrogel includes a plurality of unidirectional pores;
        a second chamber that includes a first fluid and a second fluid, wherein the second chamber includes a solid wall that separates the first fluid from the second fluid, and wherein the solid wall extends from an external wall that forms a portion of the second chamber to an outer surface of a porous membrane; and
        the porous membrane configured to separate the first chamber from the second chamber,
    wherein the solid wall is configured to move along the porous membrane as cellular extensions are projected into at least a portion of the plurality of unidirectional pores of the hydrogel.

2. The system of claim 1, wherein the porous membrane allows a component of the first or second fluid to contact the hydrogel.

3. The system of claim 1, wherein the first fluid and the second fluid comprise a cell culture medium, and wherein the first fluid has a first concentration of a substance of interest and the second fluid has a second concentration of a substance of interest such that a concentration differential exists between the first fluid and the second fluid and a concentration gradient of the substance of interest is established across the hydrogel residing in the first chamber.

4. The system of claim 3, wherein the solid wall is positioned such that the concentration gradient stimulates growth of the cellular projections into the hydrogel residing in the first chamber.

5. The system of claim 3, wherein movement of the solid wall along the porous membrane causes the concentration gradient to move along the hydrogel.

6. The system of claim 3, wherein the cell is a neural stem cell.

7. The system of claim 1, further comprising:
a reservoir that contains the first fluid; and
a pump configured to continuously circulate the first fluid between the second chamber and the reservoir to maintain a constant concentration of the first fluid.

8. The system of claim 1, wherein the first chamber comprises a first cylinder and the second chamber comprises a second cylinder, and wherein the second cylinder surrounds at least a portion of the first cylinder.

9. The system of claim 1, wherein the system comprises a layered system in which the first chamber is positioned above or below the second chamber.

10. The system of claim 1, wherein the hydrogel comprises an alginate that has been synthesized to form the plurality of unidirectional pores.

11. A method comprising:
placing a scaffold and a hydrogel in fluid communication with the scaffold into a first chamber of a tissue construct generating system, wherein the hydrogel includes a plurality of unidirectional pores;
placing a first fluid and a second fluid into a second chamber, wherein the second chamber includes a wall that separates the first fluid from the second fluid, and wherein the first chamber is separated from the second chamber by a porous membrane; and
moving the wall along the porous membrane as a cell from the scaffold extends projections into at least one of the plurality of unidirectional pores of the hydrogel.

12. The method of claim 11, wherein the first fluid and the second fluid comprise a cell culture medium, and wherein the first fluid has a first concentration of a substance of interest and the second fluid has a second concentration of a substance of interest such that a concentration differential exists between the first fluid and the second fluid and a concentration gradient of the substance of interest is established across the hydrogel residing in the first chamber.

13. The method of claim 12, wherein moving the wall comprises positioning the wall such that the concentration gradient stimulates the extension of cellular projections.

14. The method of claim 12, wherein movement of the wall along the porous membrane causes the concentration gradient to move along the hydrogel.

15. The method of claim 11, further comprising circulating the first fluid between the second chamber and a reservoir to maintain a constant concentration of the first fluid.

16. The method of claim 11, further comprising synthesizing an alginate to form the hydrogel with the plurality of unidirectional pores.

17. A kit for generating tissue comprising:
a hydrogel;
a scaffold;
a first fluid;
a second fluid;
and a bioreactor that comprises:
first means for receiving the scaffold and the hydrogel, wherein the hydrogel includes a plurality of unidirectional pores;
second means for receiving the first fluid and the second fluid, wherein the second means for receiving the first fluid and the second fluid includes a solid wall that separates the first fluid from the second fluid, and wherein the solid wall extends from an external wall that forms a portion of the second means for receiving to an outer surface of a porous means for separating the first means for receiving from the second means for receiving; and
the porous means for separating the first means for receiving from the second means for receiving,
wherein the solid wall is configured to move along the porous means for separating as cells are grown in at least a portion of the plurality of unidirectional pores of the hydrogel.

18. The kit of claim 17, wherein the first fluid and the second fluid comprise a chemical fluid, and wherein the first fluid has a first concentration of a substance of interest and the second fluid has a second concentration of a substance of interest such that a concentration differential exists between the first fluid and the second fluid and a concentration gradient of the substance of interest is established across the hydrogel residing in the first means for receiving.

19. The kit of claim 18, wherein movement of the solid wall along the porous means for separating causes the concentration gradient to move along the hydrogel.

\* \* \* \* \*